United States Patent [19]

Lyons et al.

[11] 4,332,963

[45] Jun. 1, 1982

[54] SELECTIVE PRODUCTION OF PHENYLENE DIACETATE

[75] Inventors: James E. Lyons, Wallingford; Chao-Yang Hsu, Media, both of Pa.

[73] Assignee: Sun Tech, Inc., Philadelphia, Pa.

[21] Appl. No.: 262,157

[22] Filed: May 11, 1981

Related U.S. Application Data

[63] Continuation-in-part of Ser. No. 137,707, Apr. 7, 1980, abandoned.

[51] Int. Cl.³ ............................................. C07C 69/035
[52] U.S. Cl. ................................................... 560/131
[58] Field of Search ...................... 560/131, 130, 144

[56] References Cited

U.S. PATENT DOCUMENTS 3,725,462  4/1973  Boldt et al. ..................... 560/131

OTHER PUBLICATIONS

Eberson et al., Acta Chemica Scandinavica B30, pp. 361–364, (1976).

*Primary Examiner*—Joseph E. Evans
*Attorney, Agent, or Firm*—J. Edward Hess; Donald R. Johnson; Patrick C. Baker

[57] ABSTRACT

Paraphenylene diacetate is the predominant product when phenylacetate, acetic acid and acetic anhydride are reacted in the presence of palladium and a gas mixture containing an inert gas and no more than 13 vol.% oxygen.

10 Claims, No Drawings

SELECTIVE PRODUCTION OF PHENYLENE DIACETATE

RELATED APPLICATIONS

This application is a continuation-in-part of U.S. Application Ser. No. 137,707 filed Apr. 7, 1980 and abandoned as of the filing of this application.

The subject matter of this application is related to U.S. Application Ser. No. 137,708, filed Apr. 7, 1980 and to a copending continuation-in-part application thereof, filed simultaneously with this application, entitled "Palladium Catalyzed Oxy-Acetylation of Phenyl Acetate to Meta-Acetoxyacetophenone."

BACKGROUND OF THE INVENTION

This invention relates to a process for the preparation of phenylene diacetate. More particularly the invention relates to the conversion of phenyl acetate to phenylene diacetate by a palladium catalyst in the presence of oxygen, acetic anhydride and acetic acid at elevated temperatures and pressures. Still more particularly the invention relates to a method of preparing para-phenylene diacetate as a major product. Phenylene diacetate may have utility as a solvent. Preparation of phenyl acetate is disclosed in U.S. Pat. No. 4,156,783.

The acetoxylation of chlorobenzene by Pd(OAc)$_2$ in acetic acid with an oxygen atmosphere and with and without the presence of NO$_2$ and with meta-selectivity is reported in *Acta Chemica Scandinavica* B28 (1974) 771-776, L. Eberson, et al. "Ac" as used herein refers to the acetyl group,

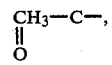

and "OAc" means the acetoxy group,

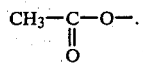

The latter reference also discloses the stoichiometric acetoxylation of phenyl acetate by 2,2'-Bipy Pd(OAc) (NO$_3$) in acetic acid at 115° C. in an oxygen atmosphere with meta-diacetoxybenzene (meta-phenylene diacetate) being the major product (60%) after a reaction period of 2 hours. The aforementioned reference, pages 597–602, states that a heterogenous gas phase acetoxylation of a monofunctional benzene derivative that takes place in acetic acid in the presence of oxygen shows a reversal of the normal substituent effect, i.e., ortho-, para-directing substituents give predominantly meta-acetoxylation and meta-directing ones give ortho-, para-acetoxylation.

Formation of methylbenzylacetate via the homogeneous reaction between palladium(II) acetate and para-xylene in acetic acid in the presence of oxygen has been studied and reported in articles in Acta Chemica Scandinavica 27, 1973, L. Eberson et al., pages 1162–1174, 1249–1254, 1255–1267. The acetoxylation of phenyl acetate by potassium peroxydisulfate with Pd(II) as a catalyst in the presence of acetic acid to form 25% ortho-, 42% meta- and 33% para-isomers of phenylene diacetate is disclosed in *Acta Chemica Scandinavica* B30 (1976) pages 361–364, Eberson et al.

The use of palladium(II) (along with other components such as oxidants, cooxidants) to catalyze aromatic acetoxylation is reported in the literature as exemplified by U.S. Pat. No. 3,772,383; *Tetrahedron Letters* No. 58, pp. 6123–6126, 1968, C. H. Bushweller; J. Org. Chem., Vol. 36, No. 14, 1971, P. M. Henry; and *J.S.C. Chem. Comm.* 1974, pages 885–886, L. Eberson et al.

The acetoxylation of benzene to phenyl acetate using oxygen, palladium on silica or alumina in the presence of acetic acid is reported in *Erdol Und Kohle*, 23, 79, 1970.

According to *Journal of Organic Chemistry*, Vol. 33, Nov. 11, 1968, D. R. Bryant et al., acetoxylation of toluene in the presence of oxygen palladium acetate and an alkali metal carboxylate at elevated temperatures results in a benzyl acetate and at higher conversions, benzylidene diacetate.

However, none of the previously mentioned references disclose or suggest the conversion of phenyl acetate to phenylene diacetate via applicants' method. Further, contrary to the previously discussed reference (Acta Chemica Scandinavica B-28, pages 597–602 and pages (771–776), applicants' method yields predominantly the para-phenylene diacetate isomer.

SUMMARY

The process of this invention comprises reacting at elevated temperature and pressure, phenyl acetate, acetic anhydride and acetic acid in the presence of a palladium catalyst and a gas mixture, which gas mixture contains an inert gas and no more than 13 volume % oxygen, to yield phenylene diacetate in accordance with the following reaction:

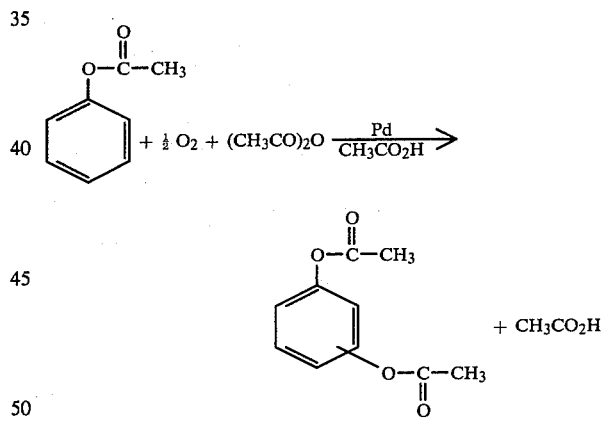

Since either acetic acid or acetic anhydride, or both, can be the source of the second acetoxy group which bonds to the phenyl acetate, the foregoing reaction scheme is merely representative of the possible reactions which may occur. Para-phenylene diacetate is the predominant product followed by the ortho- and meta-isomers.

DETAILED DESCRIPTION

"Acetoxylation" as used in this specification refers to the addition of a second acetoxy group,

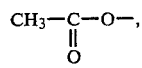

to phenyl acetate.

The process of the invention is conveniently carried out in liquid phase under acetoxylation conditions, that is, at temperatures, pressures and oxyen levels which favor the formation of phenylene diacetate. Elevated temperatures of from about 100° C. to about 300° C. are preferred and more preferably from about 150° C. to about 250° C. Reaction pressures of from about 100 psig up to about 1500 psig are preferred. The reaction time may vary considerably, depending in part on the operating conditions, including, for example, catalyst, relative concentrations of materials, and the temperature and pressure. The process can be carried out in a batch, continuous or semi-continuous system.

The amount of acetic acid is not critical. A preferred range is from about 0.2 to about 5.0 moles per mole of phenyl acetate. The acetic anhydride desirably should be present in the amount of about 0.1 to about 3 times by weight of the phenyl acetate, with 0.3 to 1.5 preferred. The molar ratio of palladium catalyst to phenyl acetate is in the range of from about 0.0001 to about 1, with 0.001 to 0.5 preferred.

The amount of oxygen is an acetoxylation amount, that is, an amount which favors the formation of phenylene diacetates, desirably the para-isomer, rather than the acetoxyacetophenone of the copending application referred to above. Generally the oxygen is used in admixture with an inert gas such as nitrogen. The oxygen content of the gas mixture should be maintained at a low concentration, for example, not more than 13 volume %, preferably about 1–8 volume %, most preferably about 3–5 volume %. Above 13 volume % the oxyacetylation reaction of the copending application will dominate.

The palladium catalyst desirably is palladium on alumina. Other palladium catalysts, e.g., palladium acetate and palladium on other supports, e.g., carbon and silica, which would result in an effective reaction mixture, can be used.

Generally, the method of the invention converts phenyl acetate substantially to phenylene diacetate with the para-isomer the predominant isomer. While a product other than phenylene diacetate may be produced, the amount of other product will be minor, if not merely a trace. The selectivity as to para-phenylene diacetate is also substantial. As shown in the Example, 82% of the isomers was the para isomer.

The following example is illustrative of the invention described herein.

EXAMPLE

A reaction was run in a stirred stainless steel autoclave using 5% palladium on alumina (2.35 mmoles) as the catalyst and as the reaction mixture a mixture of acetic anhydride (510 mmoles), phenyl acetate (950 mmoles) and acetic acid (4200 mmoles). The autoclave was heated to 200° C. under nitrogen (800 psig). Then an acetoxylation gas, 4% $O_2$ and 96% $N_2$, was passed through the heated mixture for 2.5 hours at a rate of 2 liters per minute (800 psig). At the end of the run the autoclave was cooled to room temperature and the products were analyzed by gas chromatography. Total product yield was 800% based on Pd. By gas chromatograph three products were detected: ortho-phenylene diacetate 14% selectivity, meta-phenylene diacetate 4% selectivity and para-phenylene diacetate 82% selectivity. Only a trace of acetylation product was found. The phenylene diacetates can be recovered and separated by known methods such as distillation and/or crystallization. "Selectivity" as used herein means the mole percent of one isomer to all products formed.

The foregoing yields indicate that the para-isomer is the major diacetate product while the ortho-isomer is a minor diacetate product. The meta-isomer is present in a nominal amount. These amounts can be modified by changes in operating conditions; however, conditions outside those of the present invention generally favor the para-isomer as the predominant isomer formed.

Use of other palladium catalysts, e.g., palladium acetate, and use of other operating conditions result in analogous yields and selectivities.

We claim:

1. A process for the acetoxylation of phenyl acetate, which comprises reacting, at elevated temperature and pressure and in the presence of a palladium catalyst and a gas mixture comprising an inert gas and oxygen, a reaction mixture comprising phenyl acetate, acetic acid and acetic anhydride, the amount of oxygen in the gas mixture not exceeding 13 vol. %, whereby paraphenylene diacetate is produced as the predominant product.

2. Process according to claim 1 wherein the pressure ranges up to about 1500 psig.

3. Process according to claim 1 wherein the temperature is from about 100° C. to about 300° C.

4. Process according to claim 1 wherein the molar ratio of catalyst to phenyl acetate is from about 0.0001 to about 1.

5. Process according to claim 1 wherein the amount of acetic anhydride is from about 0.1 to about 3 times by weight of the phenyl acetate.

6. Process according to claim 1 wherein the amount of oxygen in the gas mixture is about 1% to about 8 vol.%.

7. Process according to claim 1 wherein the amount of oxygen in the gas mixture is about 4 vol.%.

8. Process according to claim 1 wherein the palladium catalyst is selected from the group consisting of palladium on alumina, palladium acetate, palladium on silica, palladium acetate on silica and palladium on carbon.

9. Process according to claim 1 wherein the temperature is about 100° C. to about 300° C., the amount of acetic anhydride is from about 0.1 to about 3 times by weight of the phenyl acetate, the molar ratio of catalyst to phenyl acetate is from about 0.0001 to about 1, and the amount of oxygen in the gas mixture is about 1–8 vol.%.

10. Process according to claim 9 wherein the catalyst is palladium on a support.

* * * * *